United States Patent
Zhang et al.

(10) Patent No.: US 10,787,715 B2
(45) Date of Patent: Sep. 29, 2020

(54) METHODS FOR CULTURE AND IDENTIFICATION OF MYCROBACTERIUM AVIUM SUBSPECIES IN CROHN'S DISEASE

(71) Applicant: PZM Diagnostics, LLC, Charleston, WV (US)

(72) Inventors: Peilin Zhang, Charleston, WV (US); Lawrence M. Minardi, Charleston, WV (US)

(73) Assignee: PZM DIAGNOSTICS, LLC, Charleston, WV (US)

( * ) Notice: Subject to any disclaimer, the term of this patent is extended or adjusted under 35 U.S.C. 154(b) by 399 days.

(21) Appl. No.: 15/819,155

(22) Filed: Nov. 21, 2017

(65) Prior Publication Data

US 2018/0105868 A1    Apr. 19, 2018

Related U.S. Application Data

(62) Division of application No. 14/803,511, filed on Jul. 20, 2015, now abandoned.

(51) Int. Cl.

| | |
|---|---|
| *C12Q 1/00* | (2006.01) |
| *C12Q 1/689* | (2018.01) |
| *G01N 33/569* | (2006.01) |
| *C12N 1/20* | (2006.01) |
| *C12Q 1/6883* | (2018.01) |
| *C12Q 1/04* | (2006.01) |

(52) U.S. Cl.
CPC .............. *C12Q 1/689* (2013.01); *C12N 1/20* (2013.01); *C12Q 1/045* (2013.01); *C12Q 1/6883* (2013.01); *G01N 33/5695* (2013.01); *G01N 2333/35* (2013.01); *G01N 2469/20* (2013.01)

(58) Field of Classification Search
CPC ........................................................ C12Q 1/689
See application file for complete search history.

(56) References Cited

U.S. PATENT DOCUMENTS

| 6,235,487 B1 | 5/2001 | Holland |
| 7,488,580 B1 | 2/2009 | Naser |
| 9,005,899 B2 | 4/2015 | Liu et al. |
| 2003/0175725 A1* | 9/2003 | Kapur ................ C12Q 1/689 435/6.15 |
| 2013/0012602 A1 | 1/2013 | Haritunians et al. |

FOREIGN PATENT DOCUMENTS

EP    0489392    6/1992

OTHER PUBLICATIONS

Kiehn et al (Journal of Clinical Microbiology vol. 21, No. 4, pp. 647-648) (Year: 1985).*
Keller et al (Journal of Clinical Microbiology vol. 40, No. 5, pp. 1869-1872) (Year: 2002).*
No Author; eBioscience Flow Cytometry Best Protocols; online publication pp. 1-4) (Year: 2013).*
No Author; eBioscience Flow Cytometry Staining Buffer; online publication pp. 1-2) (Year: 2013).*
Ghodbane et al., Dramatic reduction of culture time of Mycobacterium tuberculosis, Scientific Reports, 4 : 4236, Feb. 28, 2014, 13 pages.
Markesich et al., Progress in Culture and Subculture of Spheroplasts and Fastidious Acid-Fast Bacilli Isolated from Intestinal Tissues, Journal of Clinical Microbiology, Aug. 1988, p. 1600-1603.
Schaefer et al., Effect of Oleic Acid on Growth and Cell Structure of Mycobacteria, Journal of Bacteriology. Nov. 1965, 10 pages.
BD-OADC, Becton Dickinson Middlebrook Media, Manual, 2009, 7 pages.
BD-7H9, Becton Dickinson Middlebrook Media, Manual, 2009, 7 pages.

* cited by examiner

*Primary Examiner* — Albert M Navarro
(74) *Attorney, Agent, or Firm* — Andrew D. Wright; Roberts Calderon Safran & Cole, P.C.

(57) ABSTRACT

Method and media for diagnosing Crohn's disease are provided. A method of diagnosing Crohn's disease in patients includes: obtaining a sample from an individual; culturing the sample to determine the presence or absence of *Mycobacterium avium* subspecies *hominissuis* (MAH) in the sample; and diagnosing the individual with Crohn's disease based on the determining the presence of MAH in the sample.

17 Claims, 6 Drawing Sheets

Specification includes a Sequence Listing.

10X

20X

40X

100X AFB

Acid-fast stain of the blood culture Oil X 1000

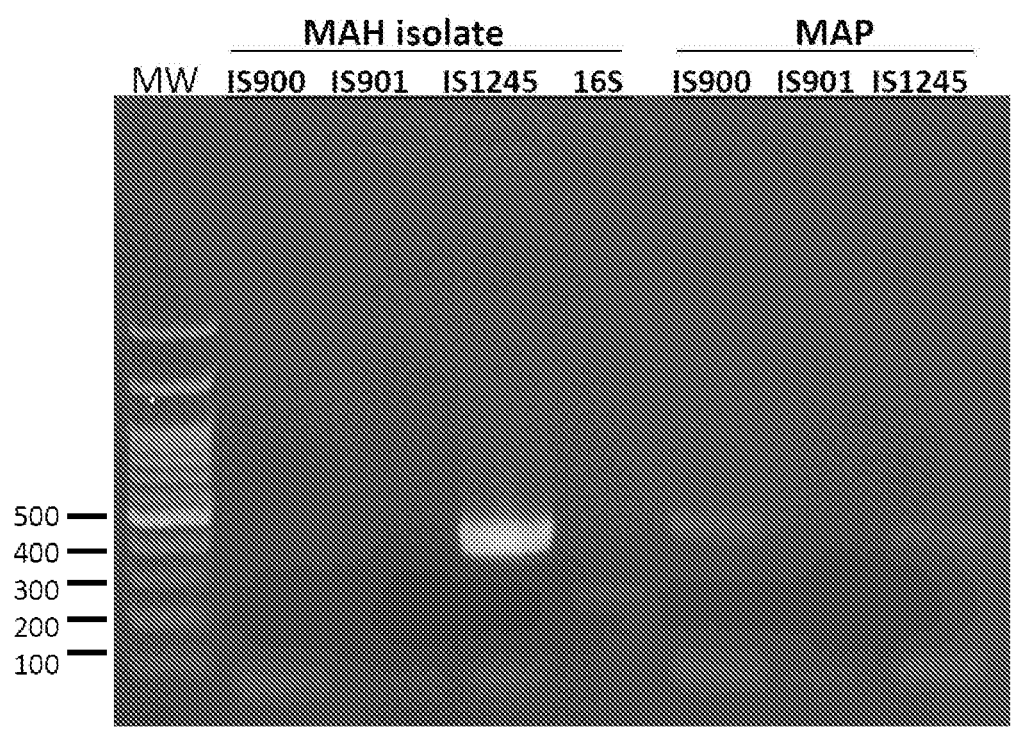
Figure 3: Gel electrophoresis of PCR results of MAH isolate

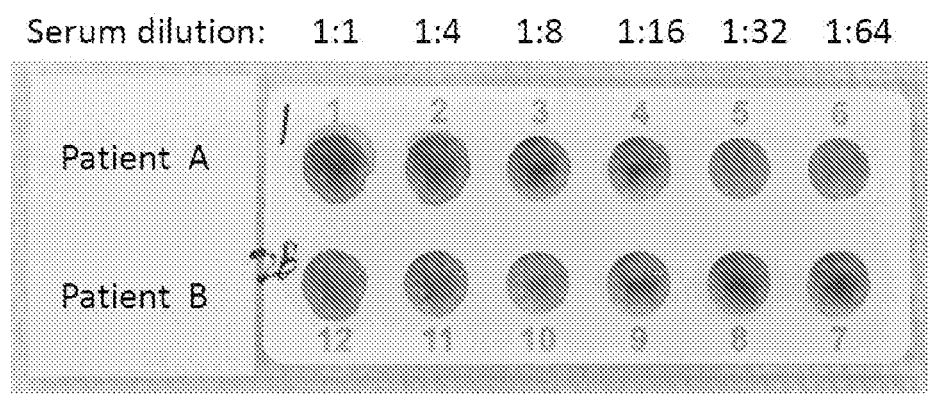
Figure 4: Modified ELISA assay using slide format for patient testing.

Figure 5:   PCR Primer sequences  5'—3'

IS901F   GGA TTG CTA ACC ACG TGG TG
IS901R   GCG AGT TGC TTG ATG AGC G

IS1245F  GAG TTG ACC GCG TTC ATC G
IS1245R  CGT CGA GGA AGA CAT ACG G

16S-F    GAG GAA GGT GGG GAT GAC G
16S-R    AGG CCC GGG AAC GTA TTC AC

IS900F   CTT TCT TGA AGG GTG TTC GG
IS900R   GAG GTC GAT CGC CCA CGT GA

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggattgctaa ccacgtggtg                                                    20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcgagttgct tgatgagcg                                                     19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gagttgaccg cgttcatcg                                                     19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgtcgaggaa gacatacgg                                                     19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gaggaaggtg gggatgacg                                                     19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aggcccggga acgtattcac                                                    20

```
<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctttcttgaa gggtgttcgg                                            20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaggtcgatc gcccacgtga                                            20
```

METHODS FOR CULTURE AND IDENTIFICATION OF MYCROBACTERIUM AVIUM SUBSPECIES IN CROHN'S DISEASE

CROSS REFERENCE TO RELATED APPLICATIONS

The instant application is a Divisional of application Ser. No. 14/803,511, filed Jul. 20, 2015, the contents of which are incorporated by reference herein in their entirety.

SEQUENCE LISTING

The instant application contains a Sequence Listing which has been submitted electronically in ASCII format and is hereby incorporated by reference in its entirety. Said ASCII copy is named "6219-40004_Sequence_Listing_ASCII.txt" and is 2,108 bytes in size.

FIELD OF THE INVENTION

The invention generally relates to the field of inflammatory diseases and, more particularly, to methods and cultures used for diagnosing Crohn's disease.

BACKGROUND

Crohn's disease is a chronic inflammatory disorder involving the gastrointestinal tract. Crohn's disease is currently considered an idiopathic autoimmune conditions, and immune suppressants are generally used in the treatment of the disease (1). In the past 60 years, many investigators have sought a pathogen(s) causing the disease, and various bacteria and viruses have been isolated and reported (2-4). For many years, *Mycobacterium avium* subspecies *paratuberculosis* (MAP), a known pathogen in Johne's disease, a chronic wasting condition in cattle and sheep (5) has been suspected to cause Crohn's disease (6). For example, U.S. Pat. No. 7,488,580 issued to Naser, discloses a method of diagnosing inflammatory bowel disease (including Crohn's disease) by detecting MAP. The role of MAP in Crohn's disease is controversial (7, 8) but two meta-analyses have concluded that a majority of patients with Crohn's disease have evidence of MAP infection (9, 10).

SUMMARY

MAP is a notoriously slow grower under the routine cultural conditions (6, 11). Therefore, the inventors sought to develop a more rapid culture method for MAP and/or other bacteria from the blood of Crohn's patients. As a result of this effort, the inventors have cultured *Mycobacterium avium* subspecies *hominissuis* (MAH) from the blood of a Crohn's patient and, to their knowledge, are the first to report MAH isolated from a Crohn's patient. The significance of this finding is discussed. Successful isolation and identification of MAH from the blood of a Crohn's patient validated the culture methods, media preparation and analytic processes.

Aspects of the invention include methods to culture and identify the presence of *Mycobacterium avium* subspecies from the blood of Crohn's patients. Aspects of the invention include culturing and identifying a *Mycobacterium avium* subspecies *hominissuis* (MAH) from the blood of a patient with Crohn's disease using novel methods, in addition to culture and identification of *Mycobacterium avium* subspecies *paratuberculosis* (MAP). A test case involved an individual with a diagnosis of Crohn's disease for two years. The individual had been treated with corticosteroids and Humira injection for six months. A blood specimen from the individual was prepared and cultured in a specialized media for four weeks, and there was visible bacterial growth in the liquid culture media. PCR (polymerase chain reaction) analysis of the bacterial growth and subsequently direct sequencing of the PCR amplicons confirmed the presence of MAH. The test case thus resulted in a first case of MAH isolated from the blood of a patient of Crohn's Disease, and successful culture and identification of MAH validated the culture media, methods and analytic processes.

Aspects of the invention provide many improvements over the method described in U.S. Pat. No. 7,488,580 issued to Naser. For example, Naser discloses a method that detects MAP, whereas aspects of the invention are instead directed to detecting MAH. Specifically, the PCR primers described in Naser are not capable of being used to detect MAH, and can only be used to detect MAP. Moreover, Naser employs nested PCR; in contrast, implementations of the invention may be practiced using direct sequencing. Further, Naser cultures a sample of blood consisting of the buffy coat, whereas aspects of the invention culture a sample made up of blood cells and fragments that remain after removing plasma and lysing the red blood cells, as well as sediments after centrifugation. Even further, aspects of the invention use a different culture medium than that disclosed by Naser. Specifically, Naser only uses a single medium. In contrast, embodiments of the invention may be practiced by culturing the sample with three different media including a liquid medium, a solid induction medium, and a solid maintenance medium.

In an aspect of the invention, there is a method of diagnosing Crohn's disease in patients, comprising: obtaining a sample from an individual; determining the presence or absence of *Mycobacterium avium* subspecies *hominissuis* (MAH) in the sample; and diagnosing the individual with Crohn's disease based on the determining the presence of MAH in the sample.

In another aspect of the invention, there is a composition usable as a culture medium, comprising: one of Middlebrook 7H9 and Middlebrook 7H10; Yeast extract; Glycerol; Sucrose; Tween 80; Mycobactin J; Oleic acid; and NAD.

In another aspect of the invention, there is a method of serology testing, comprising: serology testing plasma of an individual to identify a specific antibody against *Mycobacterium avium* subspecies *paratuberculosis* (MAP), wherein the serology testing is performed using a 12-well glass-slide for antibody titration.

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

FIG. 3 shows gel electrophoresis of PCR results of MAH isolate in accordance with aspects of the invention.

FIG. 4 shows modified ELISA assay using slide format for patient testing in accordance with aspects of the invention.

FIG. 5 shows PCR primer sequences in accordance with aspects of the invention (SEQ ID NOS 1-8, respectively, in order of appearance).

DETAILED DESCRIPTION

Figure 1A:
FIGS. 1a-1d show histologic features of colonic biopsy (AFB, acid-fast stain) in accordance with aspects of the invention.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

The invention generally relates to the field of inflammatory diseases and, more particularly, to methods and cultures used for diagnosing Crohn's disease. According to aspects of the invention, Crohn's disease may be diagnosed in a patient by: taking a sample from a patient having symptoms of Crohn's disease; detecting the presence or absence of MAH in the sample; and diagnosing Crohn's disease in the patient based on detecting the presence of MAH in the sample. In embodiments, the detecting the presence or absence of MAH in the sample is performed using a novel culture method that uses novel recipes (e.g., compositions) of three different culture media. In implementations, the culture method involves taking a whole blood sample from the patient, removing the plasma proteins from the blood, lysing the red blood cells, and only using the cellular particles from the blood with the culture media.

Methods:

In the test case described herein, an individual with a history of Crohn's disease for two years had been in and out of hospital for flares and currently on Humira twice a month for the past six months. The individual's symptom was not fully controlled and a visit was to work up for worsening of abdominal pain and cramping. Colonoscopy was performed by the gastroenterologist, and active disease was seen during the procedure. A random colon biopsy shows chronic active colitis with cryptitis, crypt abscesses and increased lymphocytic infiltrate in the lamina propria. A blood culture was performed in the specialized media based on the Middlebrook 7H9 with supplements of OADC and mycobactin J as the following, and one species of MAH was isolated from the liquid media. The identity of the MAH was confirmed by PCR of IS1245, 16S rDNA and the direct DNA sequencing of the PCR amplicons.

Media Preparation:

There are three types of media developed in our own lab using the Middlebrook 7H9 and 7H10 (Fisher Scientific/BD Biosciences) as the basic components: liquid maintenance media or liquid media, solid maintenance media and solid induction media (plates and/or slants). The recipes of the three different media are as the following in Table 1. In embodiments, for each respective medium, the constituents listed in Table 1 are mixed in water (e.g., Mili-Q water).

TABLE 1

| (weight/volume or volume/volume) | | | | | |
|---|---|---|---|---|---|
| Liquid Media | | Solid Induction Media | | Solid Maintenance Media | |
| Middlebrook 7H9 | 0.47% | Middlebrook 7H10 | 1.9% | Middlebrook 7H10 | 1.9% |
| Yeast extract | 0.1% | Yeast extract | 0.1% | Yeast extract | 0.1% |
| Glycerol | 0.5% | Glycerol | 3% | Glycerol | 0.5% |
| Sucrose | 0.2% | Sucrose | 20% | Sucrose | 0.2% |
| Tween 80 | 0.05% | Tween 80 | 0.05% | Tween 80 | 0.05% |
| Mycobactin J | 2 µg/ml | Mycobactin J | 2 µg/ml | Mycobactin J | 2 µg/ml |
| Oleic acid | 0.1% | Oleic acid | 0.1% | Oleic acid | 0.1% |
| NAD | 20 µg/ml | NAD | 20 µg/ml | NAD | 20 µg/ml |

All the media are prepared by dissolving the various components in the Mili-Q water, and autoclaved at 121° C. for 15 minutes. The media are cooled to 55° C. before OADC (oleic acid, albumin, Dextrose, catalase, NaCl from BD Bioscience Inc, 10%) and the antibiotics mix (Azlocillin 10 µg/ml, polymyxin B 10 µg/ml, amphotericin B 10 µg/ml) are added. Media plates and/or slant tubes are made. The media is stored at 4° C. refrigerator for minimally 24 hours before use.

As used herein, Middlebrook 7H9 is a liquid growth medium comprising: Ammonium Sulfate; L-Glutamic Acid; Sodium Citrate; Pyridoxine; Biotin; Disodium Phosphate; Monopotassium Phosphate; Ferric Ammonium Citrate; Magnesium Sulfate; Calcium Chloride; Zinc Sulfate; and Copper Sulfate. As used herein, Middlebrook 7H10 is a solid growth medium comprising: Ammonium Sulfate; Monopotassium phosphate; Disodium phosphate; Sodium Citrate; Magnesium Sulfate; sodium; Zinc Sulfate; Copper Sulfate; L-Glutamic Acid (sodium salt); Ferric Ammonium Citrate; Pyridoxine Hydrochloride; Biotin; Malachite Green; and Agar. Further, as is understood by those of skill in the art, Tween 80 is another name for Polysorbate 80, and NAD stands for Nicotinamide adenine dinucleotide.

Culture Method:

The basic outlines of the methods for culture and identification of bacterial growth are the following in a stepwise manner. The detailed description of the methods is followed after the outlines.

1: Transfer 4 ml blood from the purple/lavender-top vacutainer tube to a sterile 15-ml centrifuge tube, and spin the blood in a centrifuge at 6000 g for 10 minutes at room temperature.

2: Remove the plasma using a sterile pipette and store plasma in a 2-ml microfuge tube at −20° C. for antibody titration later.

3: Add 10-ml red blood cell lysis buffer (ammonium chloride 0.8%, sodium bicarbonate 0.08% and disodium EDTA 0.037%) to the cells at room temperature, and resuspend the cells by turning the capped tube up and down several times.

4: Spin the tube at 6000 g for 10 minutes in a centrifuge, and discard the supernatant to a biohazard container.

5: Add 4-ml liquid media to the centrifuge tube, and resuspend the cell pellet by turning the capped tube up and down.

6: Remove two aliquots of 100 µl the resuspended cells in liquid media, and plant them in one solid induction plate/slant and one solid maintenance plate/slant.

7: Incubate all the culture tube and plates/slants at 37° C. for 2 weeks without additional CO2. The liquid culture tube, solid plates/slants are examined visually every week. The culture media are kept at 37° C. for minimally 12 weeks.

8: After the 2 week incubation, an aliquot of 100 µl liquid culture is removed by a sterile pipette, and the culture is transferred to a microfuge tube. The cells are collected by centrifugation at 12000 g for 5 minutes. Discard the supernatant.

9: Resuspend the cells with 500 µl acetone. In embodiments, the cells are fully resuspended at this step.

10: Collect cells by centrifugation at 12000 g for 5 minutes. Discard the supernatant.

11: Resuspend the cells in 200 µl sterile TE buffer (10 mM Tris, 1 mM EDTA, pH 7.6) by vortexing the tube, and heat the resuspended cells at 95° C. for 15 minutes.

12: Chill the tubes on ice, and use the content directly for PCR analysis.

13: If there are colonies on the solid plates/slants, a single colony can be picked by a sterile toothpick, and resuspended in 200 µl TE buffer. The bacteria in TE buffer is heated at 95° C. for 15 minute and it is directly used for PCR analysis.

DETAILED DESCRIPTION OF THE METHOD ABOVE

One 4-ml purple/lavender-top tube (EDTA or sodium citrate) of blood is transferred to 15-ml centrifuge tube and centrifuged at 6000 g for 10 minutes at room temperature to separate the plasma and the cellular components including red blood cells, white blood cells, platelets and any particles. The plasma is removed from the centrifuge tube by using sterile long tip pipette, transferred to a 2 ml Eppendorf tube and stored at −20° C. freezer for MAP antibody titration using the whole cell extract of commercial strain of MAP (MAP Dominic, ATCC cat. #43545). Sterile red blood cell lysis buffer (ammonium chloride buffer containing 0.8% ammonium chloride, 0.08% sodium bicarbonate, 0.037% disodium EDTA) is added to the centrifuge tube in 4× volume (10 ml), and the cellular blood components are resuspended in the red cell lysis buffer by turning the capped tube up and down until no visible clumps are present. The nucleated cells are collected by centrifugation at 6000 g for 10 minutes, and the lysed red cells in the supernatants are emptied to a biohazard container. The nucleated cell pellet is resuspended in a 4 ml liquid maintenance media described above. Two aliquots of the resuspended nucleated cells in liquid media are removed with sterile pipette and planted on two separate solid media plates (or slants), one for induction of cell wall deficient form of MAP/MAH (spheroplasts) on the solid induction media and one for solid maintenance media. All blood culture media are incubated at 37° C. incubator with 80% humidity without additional CO2. After 2 weeks, an aliquot (0.1 cc) of liquid culture is removed and the cellular components of the culture including the nucleated cells from the blood during the 2 weeks culture period is collected by centrifugation at 12000 g for 5 minutes. The cultured material is washed with PBS buffer (pH 7.4) once and resuspended with 100% acetone. The cultured material is collected by centrifugation at 12000 g for 5 minutes, and resuspended in 200 µl TE buffer (10 mM tris, 1 mM EDTA, pH 7.6). The resuspended bacteria is heated to 95° C. for 15 minutes and it is directly used for PCR analysis. Alternatively, proteinase K (6 units) and 0.5% SDS (final concentration) are added and incubated at 65° C. overnight. The genomic DNA is isolated by phenol/chloroform/isoamyl-alcohol extraction and alcohol precipitation as described elsewhere (12). The genomic DNA was resuspended in 200 µl TE buffer, and 1 µl genomic DNA is used for PCR amplification in 50 µl volume using primers specific for IS900, IS901, IS1245, and 16s rDNA (FIG. 5)(7, 13-15). The PCR amplification is performed using 94° C. for 30 seconds, 55° C. for 30 seconds, and 72° C. for 45 seconds for 40 cycles using the PCR Core-kit (Sigma Aldrich). The PCR amplicon is visualized on 1.2% agarose gel electrophoresis. The PCR amplicons are subjected to direct DNA sequencing analysis by Eurofins Genomics sequencing services, Louisville, Ky. and the amplified DNA sequences are submitted for BLAST analysis against Genebank nucleotide sequences at NCBI (http://blast.ncbi.nlm.nih.gov/).

The liquid and solid media cultures are kept for 12 weeks with visual examination every week. Visible growth of liquid culture or bacterial colonies on the solid media are re-examined by PCR analysis and subsequent DNA sequencing analysis.

Comment on the Above Method:

Aspects of the method described herein are different from other published methods for blood culture. Traditionally in the hospital setting, blood culture is to directly add the whole blood to blood culture media bottle or plates commercially available from various vendors. The whole blood contains the blood cells and platelets as well as the serum/plasma proteins including immunoglobulins and antibodies that may inhibit the bacterial growth. An embodiment of a method described herein removes the plasma proteins, lyses the red blood cells, and only uses the cellular particles from the blood. An embodiment of a method described herein is also superior to culturing the buffy coat layer of the blood, since aspects of the inventive method include collecting the cellular particles from the lysed red blood cells. Some microorganisms grow in the red blood cells, such as Lymes disease, and an embodiment of a culture method described herein can capture the microorganisms from the red blood cells as well as white blood cells and platelets or any microorganisms in the plasma.

An embodiment of a method described herein has been used successfully to isolate MAH and other cell wall deficient bacteria from the blood of Crohn's patients.

Serology Testing Design:

In accordance with aspects of the invention, the serology testing is to identify the presence or absence of circulating antibody against *Mycobacterium avium* subspecies *paratuberculosis* (MAP) using the whole cell extract antigens prepared from the standard human MAP isolate (MAP Dominic, ATCC #43545). The whole cell extract of MAP Dominic strain is prepared as described (16). The MAP strain is cultured using the liquid media for 4-8 weeks, and the mycobacteria are collected by centrifugation at 6000 g for 10 minutes. The cell pellet is washed once with PBS, and resuspended in 100% acetone. The cell pellet again is collected by centrifugation at 6000 g for 10 minutes, and resuspended in 1% SDS in sterile water as described (16). The total whole cell extract is stored at −20° C. freezer before using to coat the 96-well titration plate or 12-well custom made glass-slide for antibody titration as below.

The titration using the 96-well plate format is performed as described elsewhere (6). Utilization of 12-well glass slide format is new, and it is easier to wash the slides in Copland jar than the 96-well plate. The basic antigen coating, blocking, and washing using PBS buffer with Tween 20 are identical to those described (12).

Figure 1B:
Figure 1C:
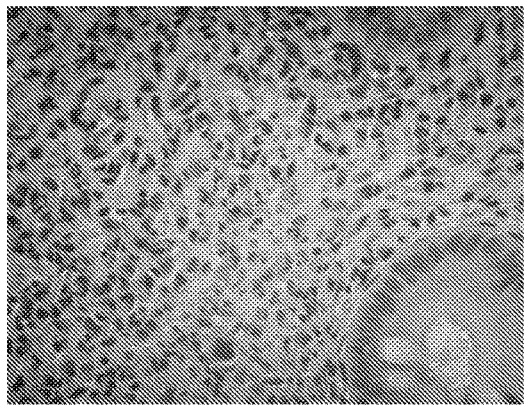
Figure 1D:
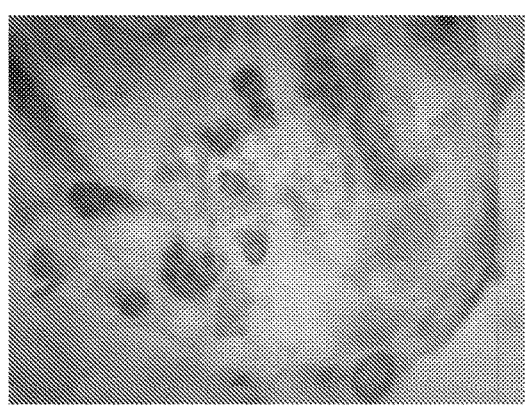
Figure 2:
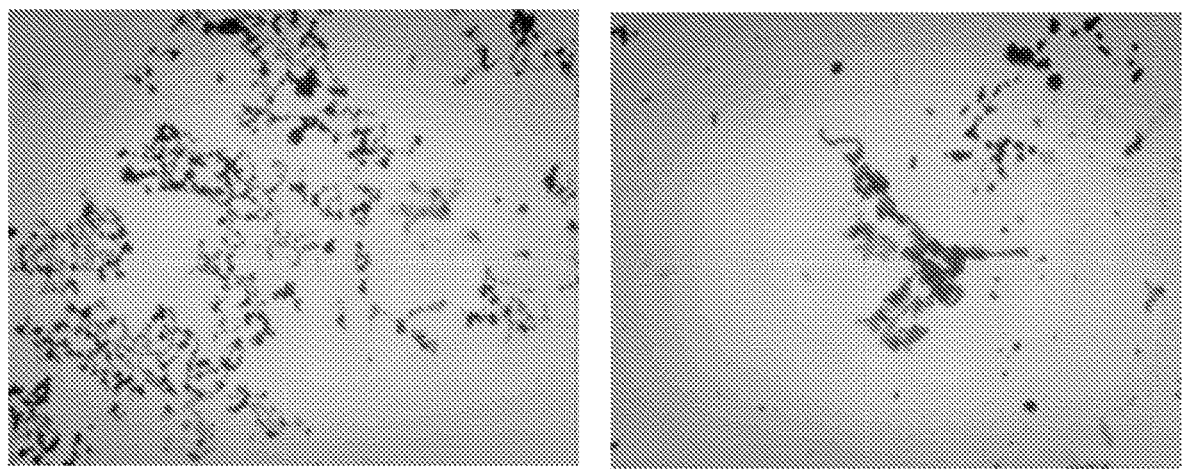
FIG. 2 shows acid-fast stain of the blood culture (Oil× 1000) in accordance with aspects of the invention.

Result:

The random colon biopsy shows chronic active colitis characterized by the presence of cryptitis, crypt abscesses and increased lymphocytic infiltrate. In addition, there are increased eosinophils within the lamina propria (FIG. 1a-c). Small loosely formed granuloma are identified. Acid fast stain is performed, and there appears to be small oval/rod acid fast bacteria within the histiocytes and the lamina propria (FIG. 1d). The histologic changes are compatible with Crohn's disease. After 4 weeks culture, a visible growth within the liquid media is present, and acid fast stain (Ziehl-Neelsen stain) reveals a spheroplast form of bacteria with partial acid-fast features (FIG. 2). PCR analysis of the isolate using primers in FIG. 5 revealed the presence of IS1245, and 16S rDNA (FIG. 3). PCR primers for 16S rDNA and IS1245 produced distinct bands (FIG. 3), and the amplicon sequence using 16s rDNA primers matched both MAP (100%, GenBank: CP010114.1) and MAH (100% GenBank AP012555.1), but the amplicon sequence using IS1245 primers only matched MAH (99%, GenBank AP012555.1). PCR using primers from IS900 was negative, indicating the isolate was not MAP. Thus, in embodiments, PCR is used to determine the presence of an MAH gene, and thus indicate MAH in the blood (sample). Based on a positive indication of MAH in the sample, the patient may be diagnosed with Crohn's diseases and treated accordingly. In addition to PCR, serology may be used to determine that there is an antibody in patient's circulation now against MAP/MAH, which may indicate the past exposure, and no MAP/MAH in the blood. There is cross-reactivity for MAP and MAH, i.e., both will react with the same antibody. Current serology cannot distinguish MAH from MAP. It is also possible that a patient may have positive PCR and not serology, or vice versa.

Serology testing of the patient's plasma using both the 96-well format and the glass-slide format showed a specific antibody against MAP/MAH whole cell antigen with a titer of 1:8. The design of the glass-slide ELISA format is showed in FIG. 4. The advantage of glass-slide format for ELISA or modified ELISA is that the slide holds much less reagent volume (20 µl in contrast to 100 µl) than the 96-well plate well. The slides are much easier to wash using a Copland jar with the washing buffer than a 96-well plate. In a clinical setting, the glass-slide format save testing time, and generate results faster.

Figure 6:
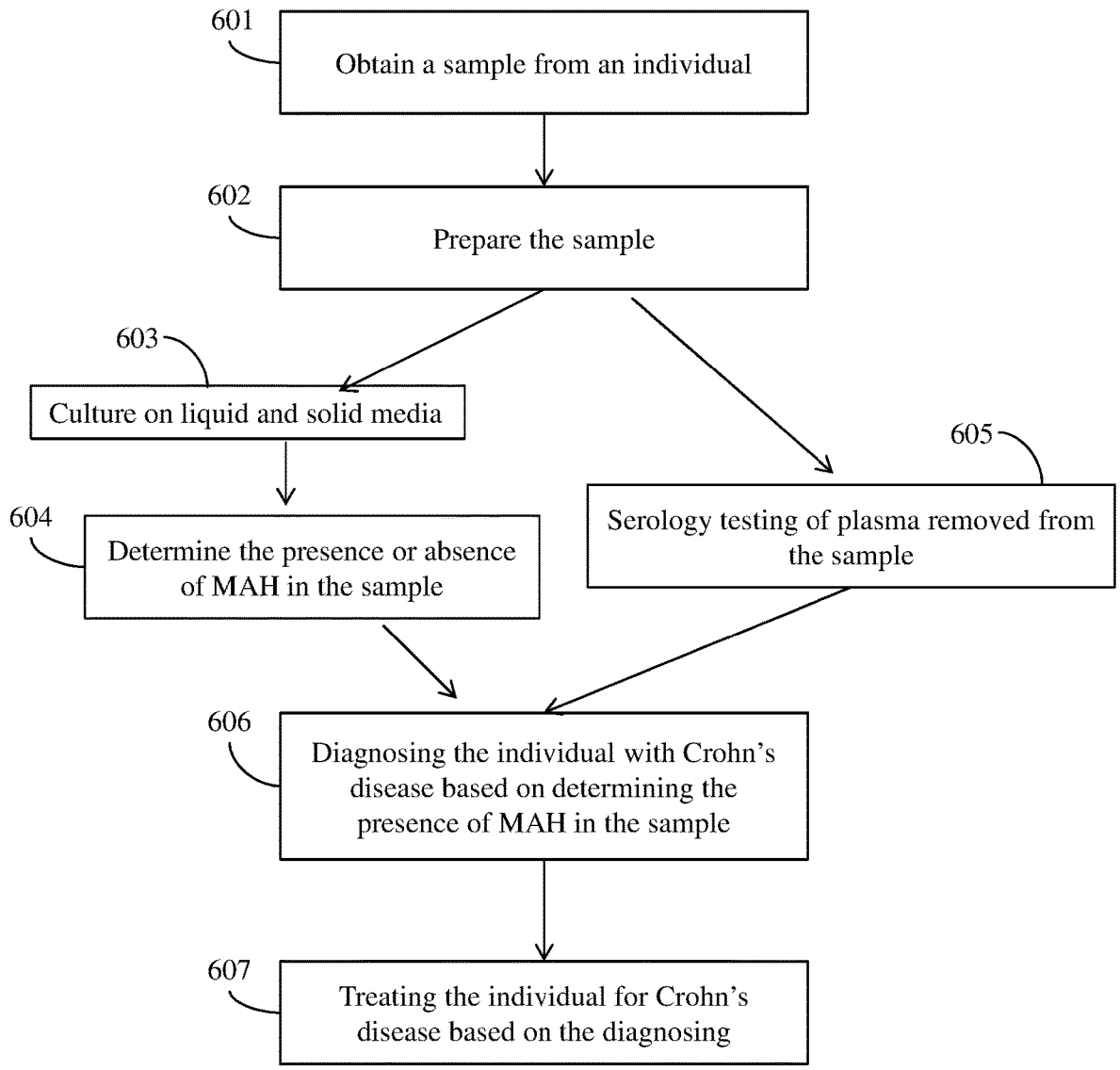
FIG. 6 shows steps of a method in accordance with aspects of the invention.

FIG. 6 shows steps of a method in accordance with aspects of the invention. Step 601 includes obtaining a sample from an individual. This may include obtaining a blood sample, such as a whole blood sample. Step 602 includes preparing the sample. In embodiments, the preparing includes removing plasma proteins from the sample; and lysing red blood cells of the sample. Step 603 includes culturing the prepared sample, e.g., after removing the plasma proteins and lysing the red blood cells. The culturing may include one or more of the steps described herein, e.g., using liquid and solid media. Step 604 includes determining the presence or absence of MAH in the (prepared) sample. In embodiments, the determining includes using PCR analysis to detect the presence of MAH gene in the sample. For example, the PCR primers described herein may be used to detect the presence of IS1245 and 16S rDNA in an isolate of the cultured sample. The determining may also include determining that the isolate is not MAP, e.g., using PCR to determine that primers from IS900 are negative. Step 605 includes serology testing of the plasma that was removed from the sample to determine the presence of a specific antibody against MAP/MAH. Step 606 includes diagnosing the individual with Crohn's disease based on the determining the presence of MAH in the sample, e.g., based on the determining. Step 607 includes treating the patient for Crohn's disease based on the diagnosing. The treating may include conventional and/or heretofore developed treatments for Crohn's disease. The treating may include providing the patient with an anti-MAH effective amount of an anti-MAH compound and a pharmaceutically acceptable excipient therefor. The anti-MAH compound may include an antibiotic, and the effective amount may be an amount sufficient to eliminate MAH from registering positive in a blood test.

Discussion

MAP has been isolated from Crohn's patients for the last 3 decades and there are conflicting data about the presence of MAP in Crohn's patients (8, 17). MAH is one of the closest members of *Mycobacterium avium* subspecies to MAP, in additional to *Mycobacterium avium* subspecies *avium* (MAA) and silvaticum (MAS)(18). MAH is present in the environment such as soil and water, and it is a known pathogen in animals such as pig, dog, deer and horse (18-20). There are reports of MAH isolates in human from the lymph nodes with lymphadenitis (21). There is no report to date of MAH from Crohn's patients to our knowledge. There is a report of MAH isolated from gastrointestinal tract of deer (22). The presence of MAH in human Crohn's patient raises questions of the role of MAH in the Crohn's disease process. It is possible that MAH is a secondary infectious agent in the patients with immune suppressants (opportunistic pathogen). It is equally possible that MAH is the pathogenic agent in this patient of clinically Crohn's disease. In fact, MAH is a more common isolate from cancer patients, but the clinical manifestation of MAH in cancer patients are mostly respiratory/pulmonary (23). Regardless the role of MAH in pathogenesis of Crohn's patient, the presence of MAH in the blood of these patients indicates a Mycobacteremia, and such a condition will require antibiotic treatment of the patients.

Genetically there are multiple gene allelic mutations susceptible for Crohn's disease, and there is a significant overlap of genetic susceptibility loci to Crohn's disease and those to mycobacteria infections (24). These genetic loci susceptible to mycobacterial infections include *Mycobacterium tuberculosis* and *Mycobacterium leprosy*. Other mycobacterial infections are possible due to the host genetic changes of Crohn's disease. It remains possible MAH is one of the causative agents of Crohn's disease.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

REFERENCES

1. Lichtenstein, G. R., Hanauer, S. B., and Sandborn, W. J. Management of Crohn's disease in adults. Am J Gastroenterol, 104: 465-483; quiz 464, 484, 2009.
2. Aronson, M. D., Phillips, C. A., Beeken, W. L., and Forsyth, B. R. Isolation and characterization of a viral agent from intestinal tissue of patients with Crohn's disease and other intestinal disorders. Prog Med Virol, 21: 165-176, 1975.
3. Parent, K. and Mitchell, P. *Pseudomonas*-like group Va bacteria in Crohn's disease. Gastroenterology, 75: 765, 1978.
4. Graham, D. Y., Markesich, D. C., and Yoshimura, H. H. Mycobacteria and inflammatory bowel disease. Results of culture. Gastroenterology, 92: 436-442, 1987.
5. Chiodini, R. J., Van Kruiningen, H. J., Merkal, R. S., Thayer, W. R., Jr., and Coutu, J. A. Characteristics of an unclassified *Mycobacterium* species isolated from patients with Crohn's disease. J Clin Microbiol, 20: 966-971, 1984.
6. Behr, M., Collins, D M Paratuberculosis: Organism, Disease, Control, First edition: CABI, 2010.
7. Naser, S. A., Ghobrial, G., Romero, C., and Valentine, J. F. Culture of *Mycobacterium avium* subspecies *paratuberculosis* from the blood of patients with Crohn's disease. Lancet, 364: 1039-1044, 2004.
8. Parrish, N. M., Radcliff, R. P., Brey, B. J., Anderson, J. L., Clark, D. L., Jr., Koziczkowski, J. J., Ko, C. G., Goldberg, N. D., Brinker, D. A., Carlson, R. A., Dick, J. D., and Ellingson, J. L. Absence of *Mycobacterium avium* subsp. *paratuberculosis* in Crohn's patients. Inflamm Bowel Dis, 15: 558-565, 2009.
9. Feller, M., Huwiler, K., Stephan, R., Altpeter, E., Shang, A., Furrer, H., Pfyffer, G. E., Jemmi, T., Baumgartner, A., and Egger, M. *Mycobacterium avium* subspecies *paratuberculosis* and Crohn's disease: a systematic review and meta-analysis. Lancet Infect Dis, 7: 607-613, 2007.
10. Abubakar, I., Myhill, D., Aliyu, S. H., and Hunter, P. R. Detection of *Mycobacterium avium* subspecies *paratuberculosis* from patients with Crohn's disease using nucleic acid-based techniques: a systematic review and meta-analysis. Inflamm Bowel Dis, 14: 401-410, 2008.
11. Chiodini, R. J., Van Kruiningen, H. J., Thayer, W. R., and Coutu, J. A. Spheroplastic phase of mycobacteria isolated from patients with Crohn's disease. J Clin Microbiol, 24: 357-363, 1986.
12. Sambrook, J., Fritsch, E. F., Maniatis, T Molecular Cloning: A Laboratory Manual, 2nd ed. edition. New York: Cold Spring Harbor Laboratory Press, 1989.
13. Jeyanathan, M., Alexander, D. C., Turenne, C. Y., Girard, C., and Behr, M. A. Evaluation of in situ methods used to detect *Mycobacterium avium* subsp. *paratuberculosis* in samples from patients with Crohn's disease. J Clin Microbiol, 44: 2942-2950, 2006.
14. Lahiri, A., Kneisel, J., Kloster, I., Kamal, E., and Lewin, A. Abundance of *Mycobacterium avium* ssp. *hominissuis* in soil and dust in Germany—implications for the infection route. Lett Appl Microbiol, 59: 65-70, 2014.
15. Relman, D. A., Loutit, J. S., Schmidt, T. M., Falkow, S., and Tompkins, L. S. The agent of bacillary angiomatosis. An approach to the identification of uncultured pathogens. N Engl J Med, 323: 1573-1580, 1990.
16. Bhaduri, S. and Demchick, P. H. Simple and rapid method for disruption of bacteria for protein studies. Appl Environ Microbiol, 46: 941-943, 1983.
17. Bull, T. J., McMinn, E. J., Sidi-Boumedine, K., Skull, A., Durkin, D., Neild, P., Rhodes, G., Pickup, R., and Hermon-Taylor, J. Detection and verification of *Mycobacterium avium* subsp. *paratuberculosis* in fresh ileocolonic mucosal biopsy specimens from individuals with and without Crohn's disease. J Clin Microbiol, 41: 2915-2923, 2003.
18. Iwamoto, T., Nakajima, C., Nishiuchi, Y., Kato, T., Yoshida, S., Nakanishi, N., Tamaru, A., Tamura, Y., Suzuki, Y., and Nasu, M. Genetic diversity of *Mycobacterium avium* subsp. *hominissuis* strains isolated from humans, pigs, and human living environment. Infect Genet Evol, 12: 846-852, 2012.
19. Campora, L., Corazza, M., Zullino, C., Ebani, V. V., and Abramo, F. *Mycobacterium avium* subspecies *hominissuis* disseminated infection in a Basset Hound dog. J Vet Diagn Invest, 23: 1083-1087, 2011.
20. Kriz, P., Jahn, P., Bezdekova, B., Blahutkova, M., Mrlik, V., Slana, I., and Pavlik, I. *Mycobacterium avium* subsp. *hominissuis* infection in horses. Emerg Infect Dis, 16: 1328-1329, 2010.
21. Kaevska, M., Slana, I., Kralik, P., Reischl, U., Orosova, J., Holcikova, A., and Pavlik, I. "*Mycobacterium avium* subsp. *hominissuis*" in neck lymph nodes of children and their environment examined by culture and triplex quantitative real-time PCR. J Clin Microbiol, 49: 167-172, 2011.
22. Glawischnig, W., Steineck, T., and Spergser, J. Infections caused by *Mycobacterium avium* subspecies *avium, hominissuis*, and *paratuberculosis* in free-ranging red deer (*Cervus elaphus hippelaphus*) in Austria, 2001-2004. J Wildl Dis, 42: 724-731, 2006.
23. Tran, Q. T. and Han, X. Y. Subspecies identification and significance of 257 clinical strains of *Mycobacterium avium*. J Clin Microbiol, 52: 1201-1206, 2014.
24. Jostins, L., Ripke, S., Weersma, R. K., Duerr, R. H., McGovern, D. P., Hui, K. Y., Lee, J. C., Schumm, L. P., Sharma, Y., Anderson, C. A., Essers, J., Mitrovic, M., Ning, K., Cleynen, I., Theatre, E., Spain, S. L., Raychaudhuri, S., Goyette, P., Wei, Z., Abraham, C., Achkar, J. P., Ahmad, T., Amininejad, L., Ananthakrishnan, A. N., Andersen, V., Andrews, J. M., Baidoo, L., Balschun, T., Bampton, P. A., Bitton, A., Boucher, G., Brand, S., Buning, C., Cohain, A., Cichon, S., D'Amato, M., De Jong, D., Devaney, K. L., Dubinsky, M., Edwards, C., Ellinghaus, D., Ferguson, L. R., Franchimont, D., Fransen, K., Gearry, R., Georges, M., Gieger, C., Glas, J., Haritunians, T., Hart, A., Hawkey, C., Hedl, M., Hu, X., Karlsen, T. H., Kupcinskas, L., Kugathasan, S., Latiano, A., Laukens, D., Lawrance, I. C., Lees, C. W., Louis, E., Mahy, G., Mansfield, J., Morgan, A. R., Mowat, C., Newman, W., Palmieri, O., Ponsioen, C. Y., Potocnik, U., Prescott, N. J., Regueiro, M., Rotter, J. I., Russell, R. K., Sanderson, J. D., Sans, M., Satsangi, J., Schreiber, S., Simms, L. A., Sventoraityte, J., Targan, S. R., Taylor, K. D., Tremelling, M., Verspaget, H. W., De Vos, M., Wijmenga, C., Wilson, D. C., Winkelmann, J., Xavier, R. J., Zeissig, S., Zhang, B., Zhang, C. K., Zhao, H., Silverberg, M. S., Annese, V., Hakonarson, H., Brant, S. R., Radford-Smith, G., Mathew, C. G., Rioux, J. D., Schadt, E. E., Daly, M. J., Franke, A., Parkes, M., Vermeire, S., Barrett, J. C. and Cho, J. H. Host-microbe interactions have shaped the genetic architecture of inflammatory bowel disease. Nature, 491: 119-124, 2012.

What is claimed:

1. A method, comprising:
centrifuging a whole blood sample obtained from an individual and removing the portion containing plasma proteins from the sample;
lysing red blood cells in the sample; and
culturing the sample in a liquid medium comprising:
Middlebrook 7H9 0.47% volume/volume;
Yeast extract 0.1% volume/volume;
Glycerol 0.5% volume/volume;
Sucrose 0.2% volume/volume;
Tween 80 0.05% volume/volume;
Mycobactin J 2 µg/ml weight/volume;
Oleic acid 0.1% volume/volume; and
NAD 20 µg/ml weight/volume.

2. A method, comprising:
centrifuging a whole blood sample obtained from an individual and removing the portion containing plasma proteins from the sample;
lysing red blood cells in the sample; and
culturing the sample in a solid medium comprising:
Middlebrook 7H10 1.9% volume/volume;
Yeast extract 0.1% volume/volume;
Glycerol 3% volume/volume;
Sucrose 20% volume/volume;
Tween 80 0.05% volume/volume;
Mycobactin J 2 µg/ml weight/volume;
Oleic acid 0.1% volume/volume; and
NAD 20 µg/ml weight/volume.

3. A method, comprising:
centrifuging a whole blood sample obtained from an individual and removing the portion containing plasma proteins from the sample;
lysing red blood cells in the sample; and
culturing the sample in a solid medium comprising:
Middlebrook 7H10 1.9% volume/volume;
Yeast extract 0.1% volume/volume;
Glycerol 0.5% volume/volume;
Sucrose 0.2% volume/volume;
Tween 80 0.05% volume/volume;
Mycobactin J 2 µg/ml weight/volume;
Oleic acid 0.1% volume/volume; and
NAD 20 µg/ml weight/volume.

4. The method of claim 1, further comprising performing serology testing of the plasma.

5. The method of claim 4, wherein the serology testing is used to identify a specific antibody against *Mycobacterium avium* subspecies *paratuberculosis* (MAP) or *Mycobacterium avium* subspecies *hominissuis* (MAH).

6. A method, comprising:
centrifuging a whole blood sample obtained from an individual and removing the portion containing plasma proteins from the sample;
lysing red blood cells in the sample; and
culturing the sample in a liquid medium and/or on a solid medium; and determining the presence of *Mycobacterium* in the sample by a method comprising the ordered steps of:
transfer an amount of the blood of the sample from a vacutainer tube to a sterile centrifuge tube, and spin the blood in a centrifuge at room temperature;
remove plasma from the centrifuge tube using a sterile pipette and store plasma in a microfuge tube at a refrigeration temperature for antibody titration later;
add red blood cell lysis buffer to the cells in the centrifuge tube at room temperature, and resuspend the cells by turning the capped centrifuge tube up and down several times;
spin the centrifuge tube in a centrifuge, and discard the supernatant;
add liquid media to the centrifuge tube, cap the centrifuge tube, and resuspend the cell pellet by turning the capped centrifuge tube up and down;
remove aliquots of the resuspended cells in liquid media, and plant them in one solid induction plate/slant and one solid maintenance plate/slant;
incubate all the culture tube and plates/slants at a temperature above room temperature without additional CO2;
after the incubating, remove an aliquot of liquid culture by a sterile pipette, transfer the culture to a microfuge tube, collect the cells by centrifugation, and discard the supernatant;

resuspend the cells with acetone, such that the cells are fully resuspended;
collect cells by centrifugation, and discard the supernatant;
resuspend the cells in sterile TE buffer by vortexing the tube, and heat the resuspended cells; and
chill the tubes, and use the content directly for PCR analysis.

7. A method, comprising:
centrifuging a whole blood sample obtained from an individual and removing the portion containing plasma proteins from the sample;
lysing red blood cells in the sample; and
culturing the sample in a liquid medium and/or on a solid medium; and determining the presence of *Mycobacterium* in the sample by ordered steps comprising:
transfer 4 ml blood of the sample from a vacutainer tube to a sterile 15-ml centrifuge tube, and spin the blood in a centrifuge at 6000 g for 10 minutes at room temperature;
remove plasma from the centrifuge tube using a sterile pipette and store plasma in a 2-ml microfuge tube at −20° C. for antibody titration later;
add 10-ml red blood cell lysis buffer to the cells in the centrifuge tube at room temperature, and resuspend the cells by turning the capped centrifuge tube up and down several times;
spin the centrifuge tube at 6000 g for 10 minutes in a centrifuge, and discard the supernatant to a biohazard container;
add 4-ml liquid media to the centrifuge tube, and resuspend the cell pellet by turning the capped centrifuge tube up and down;
remove two aliquots of 100 μl the resuspended cells in liquid media, and plant them in one solid induction plate/slant and one solid maintenance plate/slant;
incubate all the culture tube and plates/slants at 37° C. for 2 weeks without additional CO2, wherein the liquid culture tube, solid plates/slants are examined visually every week, and wherein the culture media are kept at 37° C. for minimally 12 weeks;
after the incubating, an aliquot of 100 μl liquid culture is removed by a sterile pipette, and the culture is transferred to a microfuge tube, the cells are collected by centrifugation at 12000 g for 5 minutes, and discard the supernatant;
resuspend the cells with 500 μl acetone, such that the cells are fully resuspended;
collect cells by centrifugation at 12000 g for 5 minutes, discard the supernatant;
resuspend the cells in 200 μl sterile TE buffer by vortexing the tube, and heat the resuspended cells at 95° C. for 15 minutes;
chill the tubes on ice, and use the content directly for PCR analysis; and
if there are colonies on the solid plates/slants, pick a single colony by a sterile toothpick, and resuspended in 200 μl TE buffer, the bacteria in TE buffer is heated at 95° C. for 15 minute and it is directly used for PCR analysis.

8. A method, comprising:
obtaining a sample from an individual; and
determining the presence or absence of *Mycobacterium avium* subspecies *hominissuis* (MAH) in the sample by performing the ordered steps comprising:
transfer 4 ml blood of the sample from a vacutainer tube to a sterile 15-ml centrifuge tube, and spin the blood in a centrifuge at 6000 g for 10 minutes at room temperature;
remove plasma from the centrifuge tube using a sterile pipette and store plasma in a 2-ml microfuge tube at −20° C. for antibody titration later;
add 10-ml red blood cell lysis buffer to the cells in the centrifuge tube at room temperature, and resuspend the cells by turning the capped centrifuge tube up and down several times;
spin the centrifuge tube at 6000 g for 10 minutes in a centrifuge, and discard the supernatant to a biohazard container;
add 4-ml liquid media to the centrifuge tube, and resuspend the cell pellet by turning the capped centrifuge tube up and down;
remove two aliquots of 100 μl the resuspended cells in liquid media, and plant them in one solid induction plate/slant and one solid maintenance plate/slant;
incubate all the culture tube and plates/slants at 37° C. for 2 weeks without additional CO2, wherein the liquid culture tube, solid plates/slants are examined visually every week, and wherein the culture media are kept at 37° C. for minimally 12 weeks;
after the incubating, an aliquot of 100 μl liquid culture is removed by a sterile pipette, and the culture is transferred to a microfuge tube, the cells are collected by centrifugation at 12000 g for 5 minutes, and discard the supernatant;
resuspend the cells with 500 μl acetone, such that the cells are fully resuspended;
collect cells by centrifugation at 12000 g for 5 minutes, discard the supernatant;
resuspend the cells in 200 μl sterile TE buffer by vortexing the tube, and heat the resuspended cells at 95° C. for 15 minutes; and
chill the tubes on ice, and use the content directly for PCR analysis.

9. A method, comprising:
obtaining a sample from an individual; and
determining the presence or absence of *Mycobacterium avium* subspecies *hominissuis* (MAH) in the sample by performing the ordered steps comprising:
transfer an amount of the blood of the sample from a vacutainer tube to a sterile centrifuge tube, and spin the blood in a centrifuge at room temperature;
remove plasma from the centrifuge tube using a sterile pipette and store plasma in a microfuge tube at a refrigeration temperature for antibody titration later;
add red blood cell lysis buffer to the cells in the centrifuge tube at room temperature, and resuspend the cells by turning the capped centrifuge tube up and down several times;
spin the centrifuge tube in a centrifuge, and discard the supernatant;
add liquid media to the centrifuge tube, cap the centrifuge tube, and resuspend the cell pellet by turning the capped centrifuge tube up and down;
remove aliquots of the resuspended cells in liquid media, and plant them in one solid induction plate/slant and one solid maintenance plate/slant;
incubate all the culture tube and plates/slants at a temperature above room temperature without additional CO2;

after the incubating, remove an aliquot of liquid culture by a sterile pipette, transfer the culture to a microfuge tube, collect the cells by centrifugation, and discard the supernatant;

resuspend the cells with acetone, such that the cells are fully resuspended;

collect cells by centrifugation, and discard the supernatant;

resuspend the cells in sterile TE buffer by vortexing the tube, and heat the resuspended cells; and chill the tubes, and use the content directly for PCR analysis.

10. The method of claim 6, wherein the determining is performed using PCR to detect the presence of both IS1245 and 16S rDNA.

11. The method of claim 7, wherein the determining is performed using PCR to detect the presence of both IS1245 and 16S rDNA.

12. The method of claim 8, wherein the determining is performed using PCR to detect the presence of both IS1245 and 16S rDNA.

13. The method of claim 9, wherein the determining is performed using PCR to detect the presence of both IS1245 and 16S rDNA.

14. The method of claim 2, further comprising performing serology testing of the plasma.

15. The method of claim 14, wherein the serology testing is used to identify a specific antibody against *Mycobacterium avium* subspecies *paratuberculosis* (MAP) or *Mycobacterium avium* subspecies *hominissuis* (MAH).

16. The method of claim 3, further comprising performing serology testing of the plasma.

17. The method of claim 16, wherein the serology testing is used to identify a specific antibody against *Mycobacterium avium* subspecies *paratuberculosis* (MAP) or *Mycobacterium avium* subspecies *hominissuis* (MAH).

* * * * *